United States Patent
Jakobsen et al.

(12) 
(10) Patent No.: US 6,444,434 B1
(45) Date of Patent: Sep. 3, 2002

(54) FVIIA/TF ACTIVITY INHIBITING COMPOUNDS

(75) Inventors: Palle Jakobsen, Vaerløse (DK); Egon Persson, Åkarp (SE)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/844,828

(22) Filed: Apr. 27, 2001

Related U.S. Application Data

(63) Continuation of application No. 09/616,010, filed on Jul. 13, 2000, now Pat. No. 6,238,878, which is a continuation of application No. PCT/DK00/00316, filed on Jun. 13, 2000.
(60) Provisional application No. 60/139,714, filed on Jun. 17, 1999, provisional application No. 60/141,416, filed on Jun. 29, 1999, and provisional application No. 60/152,863, filed on Sep. 8, 1999.

(30) Foreign Application Priority Data

Jun. 14, 1999 (DK) ......................................... 1999 00840
Jun. 25, 1999 (DK) ......................................... 1999 00910
Sep. 3, 1999 (DK) ......................................... 1999 01241

(51) Int. Cl.[7] .............................. C12Q 1/56; C12Q 1/00; C12Q 1/34
(52) U.S. Cl. ................................ 435/13; 435/2; 435/4; 435/18
(58) Field of Search ........................... 435/13, 2, 4, 18

(56) References Cited

U.S. PATENT DOCUMENTS

| 4,500,309 A | 2/1985 | Diederich et al. ............. 604/5 |
| 4,732,891 A | 3/1988 | Maki et al. .................... 514/21 |
| 4,736,018 A | 4/1988 | Reutelingsperger ......... 530/381 |
| 6,238,878 B1 * | 5/2001 | Jakobsen et al. ............. 435/13 |

FOREIGN PATENT DOCUMENTS

| WO | WO 91/07432 | 5/1991 |
| WO | WO 95/00541 | 1/1995 |

OTHER PUBLICATIONS

Fiore et al., Blood, vol. 80, pp. 3127–3134 (1992).
Ruf et al., Thrombosis and Haemostasis, vol. 66, pp. 529–533 (1991).
Nemerson et al., Biochemistry, vol. 25, pp. 4020–4033 (1986).
Williams et al., The Journal of Biological Chemistry, vol. 264, pp. 7536–7543 (1989).
Rao et al., Biochemistry, vol. 85, pp. 6687–6691 (1988).
Hagen et al., Biochemistry, vol. 83, pp. 2412–2416 (1986).
Thim et al., Biochemistry, vol. 27, pp. 7785–7799 (1988).

* cited by examiner

*Primary Examiner*—Louise N. Leary
(74) *Attorney, Agent, or Firm*—Reza Green, Esq.

(57) ABSTRACT

The invention relates to compounds inhibiting the activation of FX to FXa by TF/FVIIa. The compounds are anticoagulants. The invention also relates to a method of identifying a drug candidate.

5 Claims, No Drawings

FVIIA/TF ACTIVITY INHIBITING COMPOUNDS

CROSS-REFERENCE TO RELATED APPLICATIONS

This application is a continuation of U.S. application Ser. No. 09/616,010 filed on Jul. 13, 2000, now U.S. Pat. No. 6,238,878, which is a continuation of PCT/DK00/00316 filed on Jun. 13, 2000 and claims priority under 35 U.S.C. 119 of Danish application Nos. PA 1999 00840 filed on Jun. 14, 1999, PA 1999 00910 filed on Jun. 25, 1999, PA 1999 01241 filed on Sep. 3, 1999, and of U.S. provisional application Nos. 60/139,714 filed on Jun. 17, 1999, 60/141,416 filed on Jun. 29, 1999, and 60/152,863 filed on Sep. 8, 1999, the contents of which are fully incorporated herein by reference.

FIELD OF INVENTION

The present invention relates to compounds useful as TF antagonists and anticoagulants. The invention further relates to a method for identifying a drug candidate and to pharmaceutical compositions and use of the TF antagonists. The invention also relates to methods for preventing or treating FVIIa/TF-related diseases or disorders, such as the inhibition of clotting activity, tissue factor activity, and FVIIa activity as well as methods for treatment of coagulation related disease states.

Preferably, the compounds specifically block human factor X activation catalysed by the human tissue factor/factor VIIa complex (TF/FVIIa)

The compounds according to the invention are also useful in in vivo diagnostic methods and in in vitro assays, e.g., to selectively inhibit the activation of factor Xa.

BACKGROUND OF INVENTION

Blood coagulation is a process consisting of a complex interaction of various blood components, or factors, which eventually gives rise to a fibrin clot. Generally, the blood components which participate in what has been referred to as the coagulation "cascade" are proenzymes or zymogens, enzymatically inactive proteins, which are converted to proteolytic enzymes by the action of an activator, itself an activated clotting factor. Coagulation factors that have undergone such a conversion and generally referred to as "active factors", and are designated by the addition of the letter "a" to the name of the coagulation factor (e.g. FVIIa).

Activated factor X (FXa) is required to convert prothrombin to thrombin, which then converts fibrinogen to fibrin as a final stage in forming a fibrin clot. There are two systems, or pathways that promote the activation of factor X. The "intrinsic pathway" refers to those reactions that lead to thrombin formation through utilisation of factors present only in plasma. A series of protease-mediated activations ultimately generates factor IXa, which, in conjunction with factor VIIIa, cleaves factor X into Xa. FVIIa and its cofactor TF in the "extrinsic pathway" of blood coagulation effect an identical proteolysis. TF is a membrane bound protein and does not normally circulate in plasma. Upon vessel disruption, however, it is exposed and forms a complex with FVIIa to catalyse factor X activation or factor IX activation in the presence of $Ca^{2+}$ and phospholipid (Nemerson and Gentry, *Biochemistry* 25:4020–4033 (1986)). While the relative importance of the two coagulation pathways in hemostasis is unclear, in recent years FVIIa and TF have been found to play a pivotal role in the initiation and regulation of blood coagulation.

FVII is a trace plasma glycoprotein that circulates in blood as a single-chain zymogen. The zymogen is catalytically inactive (Williams et al., *J. Biol. Chem.* 264:7536–7543 (1989); Rao et al., *Proc. Natl. Acad. Sci. USA.* 85:6687–6691 (1988)). Single-chain FVII may be converted to two-chain FVIIa by factor Xa, factor XIIa, factor IXa, FVIIa or thrombin in vitro. Factor Xa is believed to be the major physiological activator of FVII. Like several other plasma proteins involved in haemostasis, FVII is dependent on vitamin K for its activity, which is required for the gamma-carboxylation of multiple glutamic acid residues that are clustered in the amino terminus of the protein. These gamma-carboxylated glutamic acids are required for the metal-associated interaction of FVII with phospholipids.

The conversion of zymogen FVII into the activated two-chain molecule occurs by cleavage of an internal Arg152-Ile 153 peptide bond (Hagen et al., *Proc. Natl. Acad. Sci. USA* 83: 2412–2416 (1986); Thim et al., *Biochemistry* 27:7785–7793 (1988)). In the presence of TF, phospholipids and calcium ions, the two-chain FVIIa rapidly activates factor X or factor IX by limited proteolysis.

It is often desirable to selectively block or inhibit the coagulation cascade in a patient. Anticoagulants such as heparin, coumarin, derivatives of coumarin, indandione derivatives, thrombin inhibitors, factor Xa inhibitors, modified FVII or other agents have previously been used.

Inhibition of coagulation is beneficial in a number of diseased states, for example during kidney dialysis, or to treat deep vein thrombosis, disseminated intravascular coagulation (DIC), atherosclerosis and a host of other medical disorders. For example, heparin treatment or extracorporeal treatment with citrate ions (U.S. Pat. No. 4,500,309) may be used in dialysis to prevent coagulation during the course of treatment. Heparin is also used in preventing deep vein thrombosis in patients undergoing surgery. Treatment with heparin and other anticoagulants may, however, have undesirable side effects. Available anticoagulants generally act throughout the body, rather than acting specifically at the site of injury, i. e. the site at which the coagulation cascade is active. Heparin, for example, may cause severe bleedings. Furthermore, with a half-life of approximately 80 minutes, heparin is rapidly cleared from the blood, necessitating frequent administrating.

Other known anticoagulants comprise thrombin and factor Xa inhibitors derived from bloodsucking organisms. Antithrombins, hirudin, hirulog and hirugen are recombinant proteins or peptides derived from the leach *Hirudo medicinalis*, whereas the factor Xa inhibitor antistatin and the recombinant derivative rTAP are ticke-drived proteins. Inhibitors of platelet aggregation such as monoclonal antibodies or synthetic peptides, which interfere with the platelet receptor GPIIb/IIIa are also effective as anticoagulants.

Bleeding complications are observed as an undesired major disadvantage of anti-thrombin, anti-factor Xa, as well as anti-platelet reagents. This side effect is strongly decreased or absent with inhibitors of the FVIIa/TF activity. Such anticoagulants comprise the physiological inhibitor TFPI (tissue factor pathway inhibitor) and modified FVII (FVIIai), which is FVIIa modified in such a way that it is catalytically inactive but still binds to TF and competes with active FVIIa.

In addition to the anticoagulants briefly described above, several naturally occurring proteins have been found to have anticoagulant activity. For example, Reutelingsperger (U.S. Pat. No. 4,736,018) isolated anticoagulant proteins from bovine aorta and human umbilical vein arteries. Maki et al.

(U.S. Pat. No. 4,732,891) discloses human placenta-derived anticoagulant proteins.

The anticoagulant FVIIai has also been shown to have effect in suppressing or preventing restenosis. Proliferation of smooth muscle cells (SMCs) in the vessel wall is an important event in the formation of vascular lesions in atherosclerosis, after vascular reconstruction or in response to other vascular injury. For example, treatment of atherosclerosis frequently includes the clearing of blocked vessels by angioplasty, endarterectomy or reduction atherectomy, or by bypass grafting. These are surgical procedures in which atherosclerotic plaques are compressed or removed through catheterization (angioplasty), stripped away from the arterial wall through an incision (endarterectomy) or bypassed with natural or synthetic grafts. These procedures remove the vascular endothelium, disturb the underlying intimal layer, and result in the death of medial SMCs. Medial SMC proliferation and migration follow this injury into the intima, which typically occurs within the first few weeks and up to six months after injury and stops when the overlying endothelial cell layer is re-established, In humans, these lesions are composed of about 20% cells and 80% extracellular matrix. In about 30% or more of patients treated by angioplasty, endarterectomy or bypass grafts, thrombosis and/or SMC proliferation in the intima causes re-occlusion of the vessel and consequent failure of the reconstructive surgery. This closure of the vessel subsequent to surgery is known as restenosis.

For long term prophylactic treatment and increased compliance it is desirable to have access to low-molecular-weight compounds which may be administered via a route other than intravenously and which have an inhibitory effect on FVIIa-TF activity similar to that of FVIIai.

Thus, there is still a need in the art for improved compositions having anticoagulant activity which can be administered orally or otherwise non-intravenously at relatively low doses and which does not produce any undesirable side effects. The present invention fulfils this need by providing anticoagulants that act specifically on FVIIa/TF/FX complex formed at sites of injury.

It is also desirable to have access to a method for identifying compounds having an inhibitory action on FVIIa/TF activity.

SUMMARY OF THE INVENTION

It has been found that the activity of FX in complex with TF/FVIIa can be inhibited by small organic compounds. By this action the initiation of blood coagulation by FX/FIIa/TF is prevented, avoiding the formation of undesired thrombi.

The present invention provides a method, which can be used for identifying compounds that can be used for the modulation of the TF/FVII induced pathway of coagulation—the method specifically identifies compounds, which inhibits the activation of FX (to FXa) by FVIIa/TF-complex.

The present invention also provides compounds, which exert their anticoagulant effect by modulating the activation of FX to FXa by TF/FVIIa. The compounds are useful for the treatment of FVIIa/TF-related diseases or disorders.

It is an object of the present invention to provide compounds having pharmacological activity as inhibitors of FVIIa/TF/FX activity.

The compounds according to the present invention hinder the TF/FVIIa activation of FX The compounds, or drug candidates, bind to TF or to FVIIa or to TF/FVIIa or to FX and thus hinder or prevent either the formation of the TF/FVIIa complex or the binding between the TF/FVIIa complex and Fx, or the binding of FX to FVII or to TF.

Structures binding to FVIIa or FXa may do this either at the active site—thus hindering the progress of the coagulation cascade—or in areas outside the active site. Preferred compounds are the ones which have low activity at the FX active site as seen from a FXa amidolytic assay screen (for example as described later in the present application) and which exhibit a medium to low effect on the FVII active site as seen from a FVIIa/TF amidolytic assay screen (for example as described later in the present application). Activity on other serine proteases should be minimal.

Preferred compounds of the invention bind to FVIIa/TF in such a way that FX is not able to effectively bind to the TF/FVIIa complex. When FX does not effectively bind to TF/FVIIa complex it is not effectively converted to its activated form, FXa. Preferred compounds of the invention can inhibit TF function by effectively blocking FX binding or access to the TF/FVIIa complex molecules.

The compounds may be identified by a method comprising the following steps:
a) testing the compound in a FX activation assay,
b) testing the compound in a FXa amidolytic assay,
c) testing the compound in a TF/FVIIa amidolytic assay,
d) selecting the compound as a compound having an inhibitory action on TF-FVII activity if
  1. the compound shows an activity in the assay of step a) corresponding to a half-maximal inhibition at a concentration of 20 $\mu$M or less in the FX activation assay described in Example 3,
  2. and showing an activity in the assay of step b) corresponding to a half-maximal inhibition at a concentration of 100 $\mu$M or more in the FXa amidolytic assay described in example 2, and
  3. showing an activity in the assay of step c) corresponding to a half-maximal inhibition at a concentration of 20 $\mu$M or more in the TF/FVIIa amidolytic assay described in Example 1.

It is also an object of the present invention to provide a method for identifying structures having the desired activity. The method for identifying compounds having an inhibitory action on FVII-TF activity comprises the following steps:
a) testing the compound in a FX activation assay,
b) testing the compound in a FXa amidolytic assay,
c) testing the compound in a TF/FVIIa amidolytic assay,
d) selecting the compound as a compound having an inhibitory action on TF-FVII activity if
  1. the compound shows an activity in the assay of step a) corresponding to a half-maximal inhibition at a concentration of 20 $\mu$M or less in the FX activation assay described in Example 3,
  2. and showing an activity in the assay of step b) corresponding to a half-maximal inhibition at a concentration of 100 $\mu$M or more in the FXa amidolytic assay described in example 2, and
  3. showing an activity in the assay of step c) corresponding to a half-maximal inhibition at a concentration of 20 $\mu$M or more in the TF/FVIIa amidolytic assay described in Example 1.

Further selection of structures having the preferred activity described above can be done by testing these structures in a TF/FVIIa induced plasma clotting assay, as described below.

Structures having a clot ratio >1 are preferred.

Structures having the preferred activity can conveniently be found by screening commercial available compound libraries which can be obtained from companies like SPECS, Maybridge, Chembridge, and Panlabs. Alternatively the structures might be synthesised inhouse.

Examples of such structures are and their activities in accordance with the preferred profile are presented in the Examples below.

These structures should only be regarded as examples on the diversity of structural substructures, which can be identified using the methods described herein, and they should in no way be regarded as an exclusive list. In one embodiment of the invention, the compounds are the compounds of Examples 5 to 22.

It is an object of the present invention to provide usage of the compounds of the present invention for the manufacture of a medicament prevention or treatment of FVIIa/TF-related diseases or disorders, including, but not limited to, deep venous thrombosis, arterial thrombosis, post surgical thrombosis, coronary artery bypass graft (CABG), percutaneous transdermal coronary angioplastry (PTCA), stroke, tumour metastasis, angiogenesis, thrombolysis, arteriosclerosis and restenosis following angioplastry, acute and chronic indications such as inflammation, septic chock, septicemia, hypotension, adult respiratory distress syndrome (ARDS), disseminated intravascular coagulopathy (DIC), pulmonary embolism, platelet deposition, myocardial infarction, or the prophylactic treatment of mammals with atherosclerotic vessels at risk for thrombosis, ex vivo FVIIa/TF related processes such as coagulation that may result from the extracorporeal circulation of blood, e.g. dialysis procedures, blood filtration, or blood bypass during surgery.

In one embodiment, the subject in need of treatment is a human.

In one aspect, the present invention provides a method for identifying a drug candidate having an inhibitory action on FVII-TF activity, the method comprising the following steps:

a) testing the compound in a FX activation assay,
b) testing the compound in a FXa amidolytic assay,
c) testing the compound in a TF/FVIIa amidolytic assay,
d) selecting the compound as a compound having an inhibitory action on TF-FVII activity if 1. the compound shows an activity in the assay of step a) corresponding to a half-maximal inhibition at a concentration of 20 $\mu$M or less in the FX activation assay described in Example 3,
2. and showing an activity in the assay of step b) corresponding to a half-maximal inhibition at a concentration of 100 $\mu$M or more in the FXa amidolytic assay described in example 2, and
3. showing an activity in the assay of step c) corresponding to a half-maximal inhibition at a concentration of 20 $\mu$M or more in the TF/FVIIa amidolytic assay described in Example 1.

In one embodiment, the method further comprises subjecting the selected compound to a FVIIa/F-initiated clotting assay and selecting compounds showing clotting activity in said assay.

In another embodiment, compounds showing an activity corresponding to a clot ratio of more than 1 in the FVIIa/TF-initiated clotting assay of Example 4, are selected.

In another aspect, the invention provides a method for inhibiting the formation of FVIIa/TF/FX complex in a subject, comprising administering a drug candidate selected as described in claim 1 to a subject in need of such treatment In one embodiment, the drug candidate substantially acts as an inhibitor of the activation of FX to FXa by TF/FVIIa.

In another aspect, the invention provides compounds with anti-coagulant activity identifiable by a method comprising the following steps:

a) testing the compound in a FX activation assay,
b) testing the compound in a FXa amidolytic assay,
c) testing the compound in a TF/FVIIa amidolytic assay,
d) selecting the compound as a compound having an inhibitory action on TF-FVII activity if 1. the compound shows an activity in the assay of step a) corresponding to a half-maximal inhibition at a concentration of 20 $\mu$M or less in the FX activation assay described in Example 3,
2. and showing an activity in the assay of step b) corresponding to a half-maximal inhibition at a concentration of 100 $\mu$M or more in the FXa amidolytic assay described in example 2, and
3. showing an activity in the assay of step c) corresponding to a half-maximal inhibition at a concentration of 20 $\mu$M or more in the TF/FVIIa amidolytic assay described in Example 1.

In one embodiment, the selected compounds are subjected to a further selection by subjecting them to a FVIIa/TF-initiated clotting assay and selecting compounds showing clotting activity in said assay.

In another embodiment, the selected compounds show an activity in the assay of step c) corresponding to a half-maximal inhibition at a concentration of 100 $\mu$M or more in the TF/FVIIa amidolytic assay described in Example 1.

In another embodiment, compounds showing an activity corresponding to a clot ratio of more than 1 in the FVIIa/TF-initiated clotting assay of Example 4, are selected.

In another aspect, the invention provides a pharmaceutical composition comprising a compound selected by the method of the invention, and optionally a pharmaceutical acceptable carrier or excipient.

In another aspect, the invention provides the use of a compound selected according to the method of the present invention for the manufacture of a medicament for prevention or treatment of a FVIIa/TF-related disease or disorder in a mammal.

In one embodiment, the FVIIa/TF-related disease or disorder is deep venous thrombosis, arterial thrombosis, post surgical thrombosis, coronary artery bypass graft (CABG), percutaneous transdermal coronary angioplastry (PTCA), stroke, tumour metastasis, angiogenesis, thrombolysis, arteriosclerosis and restenosis following angioplastry, acute and chronic indications such as inflammation, septic chock, septicemia, hypotension, adult respiratory distress syndrome (ARDS), disseminated intravascular coagulopathy (DIC), pulmonary embolism, platelet deposition, myocardial infarction, or the prophylactic treatment of mammals with atherosclerotic vessels at risk for thrombosis, ex vivo FVIIa/TF related processes such as coagulation that may result from the extracorporeal circulation of blood, e.g. dialysis procedures, blood filtration, or blood bypass during surgery.

In another aspect, the invention provides a method for treatment of a FVIIa/TF-related disease or disorder in a subject, which method comprises administering an effective amount of at least one compound selected according to the method of the present invention to a subject in need of such treatment.

In another aspect, the invention provides a method for treatment of a FVIIa/TF-related disease or disorder in a subject, which method comprises administering an effective amount of at least one drug candidate selected according to the method of the present invention to a subject in need of such treatment.

Further objects will become apparent from the following description.

DETAILED DESCRIPTION OF THE INVENTION

Definitions

As used herein "small molecules" means compounds having a molecular weight of less than 1000 Dalton, preferred are compounds having a molecular weight of less than 800 Dalton.

"Modulating and normalizing an impaired haemostatic balance" means achieving an effect on the coagulation system measurable in vitro assays and/or animal models which effect diminishes the risk for thrombosis or bleedings.

"Treatment" means the administration of an effective amount of a therapeutically active compound of the invention with the purpose of preventing any symptoms or disease state to develop or with the purpose of curing or easing such symptoms or disease states already developed. The term "treatment" is thus meant to include prophylactic treatment.

A FVIIa/TF related disease or disorder or a thrombotic or coagulopathic related disease or disorder is meant to include inflammatory responses and chronic thromboembolic diseases or disorders associated with fibrin formation including vascular disorders such as deep venous thrombosis, arterial thrombosis, post surgical thrombosis, coronary artery bypass graft (CABG), percutaneous transdermal coronary angioplastry (PTCA), stroke, tumour metastasis, angiogenesis, thrombolysis, arteriosclerosis and restenosis following angioplastry, acute and chronic indications such as inflammation, septic chock, septicemia, hypotension, adult respiratory distress syndrome (ARDS), disseminated intravascular coagulopathy (DIC), pulmonary embolism, platelet deposition, myocardial infarction, or the prophylactic treatment of mammals with atherosclerotic vessels at risk for thrombosis, and other diseases or disorders. The FVIIa/TF related disorder is not limited to in vivo coagulopatic disorders such as those named above but includes ex vivo FVIIa/TF related processes such as coagulation that may result from the extracorporeal circulation of blood, including blood removed in-line from a patient in such processes as dialysis procedures, blood filtration, or blood bypass during surgery.

"Inhibitors of FVIIa-TF activity": Compounds with the general formula I inhibit FVIIa/TF-activity in in vitro assays of amidolytic and proteolytic activity and thus are able to prolong by preventing the formation of a FVIIa/TF complex the TF-induced coagulation in human plasma. They may do so by inhibiting FVIIa activity, by inhibiting the activity of FVIIa/TF complex, by preventing the binding of FX to FVIIa/TF complex, or by preventing the activation of factor X when bound to FVIIa/TF. Compounds which solely inhibit the proteolytic activity of FVIIa/TF and/or prolong the coagulation time may do so by preventing the association of factor X with the FVIIa/TF complex or by preventing the activation of factor X bound to the complex.

The compounds may hinder the TF/FVIIa activation of FX by binding to either TF, FVII, or FX, thus hindering either the formation of the TF/FVII complex, the binding between the TF/FVIIa complex and FX, or the binding of FX to either FVII or TF.

Structures binding to FVII or FX may do this either at the active site—thus hindering the progress of the coagulation cascade—or in areas outside the active site. Preferred compounds are the ones which have low activity at the FX active site as seen from a FXa amidolytic assay screen and which exhibit a medium to low effect on the FVII active site as seen from a FVIIa/TF amidolytic assay. Activity on other serine proteases should be minimal.

In this context, the term half-maximal inhibition means reducing the activity of the respective enzyme or enzyme-cofactor complex in the absence of inhibitory compound by 50%.

"Modulators of the TF/FVIIa pathway": Compounds that modulate the coagulation process through an inhibitory action on the TF/FVIIa complex or on TF activity. The activity of FVIIa in complex with TF, in particular its activation of factor X, can be inhibited by a low-molecular weight compound. By this action, the initiation and acceleration of the blood coagulation cascade upon exposure of TF to flowing blood is prevented.

"Modulating and normalizing an impaired haemostatic balance" means achieving an effect on the coagulation system measurable in vitro assays and/or animal models which effect diminishes the risk for thrombosis or bleedings.

| Abreviations | |
|---|---|
| TF | Tissue factor |
| FVII or fVII | factor VII |
| FVIIa or fVIIa | activated factor VII |
| FVIIa-TF | complex between activated factor VII and tissue factor initiating blood coagulation |

Pharmaceutical Compositions

In another aspect, the present invention includes within its scope pharmaceutical compositions comprising; as an active ingredient, at least one of the compounds of the present invention or a pharmaceutically acceptable salt thereof together with a pharmaceutically acceptable carrier or diluent.

Optionally, the pharmaceutical composition of the invention may comprise a compound combined with one or more other compounds exhibiting anticoagulant activity, e.g., platelet aggregation inhibitor.

The compounds may be formulated into pharmaceutical composition comprising the compounds and a pharmaceutically acceptable carrier or diluent. Such carriers include water, physiological saline, ethanol, polyols, e.g., glycerol or propylene glycol, or vegetable oils. As used herein, "pharmaceutically acceptable carriers" also encompasses any and all solvents, dispersion media, coatings, antifungal agents, preservatives, isotonic agents and the like. Except insofar as any conventional medium is incompatible with the active ingredient and its intended use, its use in the compositions of the present invention is contemplated.

The compositions may be prepared by conventional techniques and appear in conventional forms, for example, capsules, tablets, solutions or suspensions. The pharmaceutical carrier employed may be a conventional solid or liquid carrier. Examples of solid carriers are lactose, terra alba, sucrose, talc, gelatine, agar, pectin, acacia, magnesium stearate and stearic acid. Examples of liquid carriers are syrup, peanut oil, olive oil and water. Similarly, the carrier or diluent may include any time delay material known to the art, such as glyceryl monostearate or glyceryl distearate, alone or mixed with a wax. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or colouring substances and the like, which do not deleteriously react with the active compounds.

The route of administration may be any route, which effectively transports the active compound to the appropriate or desired site of action, such as oral or parenteral, e.g., rectal, transdermal, subcutaneous, intranasal, intramuscular, topical, intravenous, intraurethral, ophthalmic solution or an ointment, the oral route being preferred.

If a solid carrier for oral administration is used, the preparation can be tabletted, placed in a hard gelatine capsule in powder or pellet form or it can be in the form of a troche or lozenge. The amount of solid carrier may vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

For nasal administration, the preparation may contain a compound of formula I dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet, which may be prepared by conventional tabletting techniques, contains

| Core | |
|---|---|
| Active compound (as free compound or salt thereof) | 10 mg |
| Colloidal silicon dioxide (Areosil ®) | 1.5 mg |
| Cellulose, microcryst. (Avicel ®) | 70 mg |
| Modified cellulose gum (Ac-Di-Sol ®) | 7.5 mg |
| Magnesium stearate | |
| Coating | |
| HPMC | approx. 9 mg |
| *Mywacett ® 9-40 T | approx. 0.9 mg |

*Acylated monoglyceride used as plasticizer for film coating.

The compounds of the invention may be administered to a mammal, especially a human, in need of such treatment, prevention, elimination, alleviation or amelioration of various coagulation-related diseases as mentioned above. Such mammals also include animals, both domestic animals, e.g. household pets, and non-domestic animals such as wildlife.

The compounds of the invention are effective over a wide dosage range. For example, in the treatment of adult humans, dosages from about 0.001 to about 100 mg, preferably from about 0.05 to about 100 mg per day may be used. A most preferable dosage is about 0.1 mg to about 70 mg per day. In choosing a regimen for patients, it may frequently be necessary to begin with a dosage of from about 20 to about 70 mg per day and when the condition is under control to reduce the dosage as low as from about 0.1 to about 10 mg per day. The exact dosage will depend upon the mode of administration, on the therapy desired, form in which administered, the subject to be treated and the body weight of the subject to be treated, and the preference and experience of the physician or veterinarian in charge.

Generally, the compounds of the present invention are dispensed in unit dosage form comprising from about 0.1 to about 100 mg of active ingredient together with a pharmaceutically acceptable carrier per unit dosage.

Usually, dosage forms suitable for oral, nasal, pulmonal or transdermal administration comprise from about 0.001 mg to about 100 mg, preferably from about 0.01 mg to about 50 mg of the compounds of formula I admixed with a pharmaceutically acceptable carrier or diluent.

The compounds may be administered concurrently, simultaneously, or together with a pharmaceutically acceptable carrier or diluent, whether by oral, rectal, or parenteral (including subcutaneous) route. The compounds are often, and preferably, in the form of an alkali metal or earth alkali metal salt thereof.

Suitable dosage ranges varies as indicated above depending upon the exact mode of administration, form in which administered, the indication towards which the administration is directed, the subject involved and the body weight of the subject involved, and the preference and experience of the physician or veterinarian in charge.

ASSAYS

Methods for Identifying Inhibitory Compounds

The general strategy for identifying compounds is depicted below:

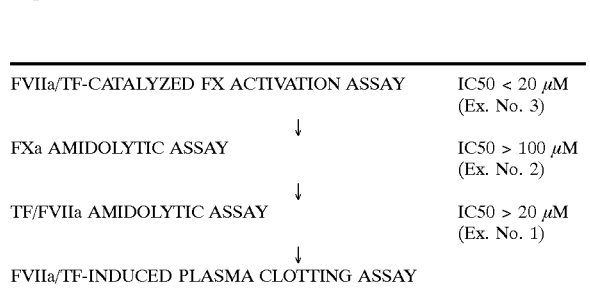

Inhibitory Compounds are Identified in a FX Activation Assay:

The compounds are dissolved in DMSO and mixed with a solution of FVIIa in $Ca^{2+}$-containing buffer (1+5). 30 μl of this mixture was then mixed with 45 μl TF (relipidated in PC/PS vesicles) and 25 μl of a solution containing FX, all in $Ca^{2+}$-containing buffer. This gives final concentrations of 100 pM FVIIa, 5 pM TF, 175 nM FX and various concentrations of the compounds. After a 5-min incubation, the FVIIa/TF-catalyzed activation of FX is terminated by the addition of 50 μl buffer containing enough EDTA to give an excess over the Ca2+ ions present. 50 μl of a 2-mM solution of S-2765 (FXa substrate) is then added and the FXa formed is allowed to hydrolyze the substrate for 10 minutes during which the absorbance at 405 nm is continuously monitored in a SPECTRAmax™ 340 plate reader. The slope of the absorption curve is compared to that of a control where DMSO alone was added to FVIIa/TF/FX.

Test of Anticoagulant Potency in a FVIIa/TF-initiated Clotting Assay:

The test compounds, 20 mM in DMSO, are diluted in citrated normal human plasma just before the analysis (1+19) and placed in the sample carousel. 55 μl sample (compound in plasma) is mixed with 55 μl of thromboplastin (Innovin, Dade) and incubated for 5 min. The clotting reaction is started by adding 55 μl of a 25-mM $CaCl_2$ solution, yielding a final compound concentration of 0.33 mM. The clotting time is measured using an ACL 300 R coagulometer. The ratio between the clotting time in the presence and absence of test compound is used to quantify the anticoagulant efficiency.

Counterscreening Assays to Eliminate Compounds Directed Towards the Active Site of FVIIa or FXa (the FVIIa/TF Amidolytic Assay also Detects Compounds Interfering with FVIIa/TF Complex Assemble):

a) FVIIa/TF Amidolytic Assay:

Compound solutions and buffer are the same as in the above FX activation assay. 150 microliters of FVIIa (13.3 nM in buffer), 20 microliters of soluble TF. (250 nM in buffer), 10 microliters of test compound (various concentrations in DMSO) and 20 microliters of substrate S-2288 (10 mM in water) is mixed in microtiter plate well. This gives final concentrations of FVII(a, TF and S-2288 of 10 nM, 25 nM and 1 mM, respectively. The absorbance at 405 nm is measured continuously for 20 minutes. The degree of inhibition is calculated from the slope of the absorbance curve compared to the curve obtained when using DMSO without test compound.

b) FXa Amidolytic Assay:

Compound solutions and buffer are the same as in the above FX activation assay. 170 microliters of FXa (1.17 nM in buffer), 10 microliters of test compound (various concentrations in DMSO) and 20 microliters of substrate S-2765 (10 mM in water) is mixed in a microtiter plate well. This gives-final concentrations of FXa and S-2765 of 1 nM and 1 mM, respectively. The absorbance at 405 nm is measured continuously for 20 minutes. The degree of inhibition is calculated from the slope of the absorbance curve compared to the curve obtained when using DMSO without test compound.

Pharmacological Properties

The compounds of this invention can be used to modulate and normalise an impaired haemostatic balance in mammals caused by deficiency or malfunction of blood clotting factors or their inhibitors. The FVIIa and in particular the FVIIa/TF activity plays an important role in the control of the coagulation cascade, and modulators of this key regulatory activity such as the present invention can be used in the treatment of coagulation-related diseased states.

The pharmaceutical composition according to the invention is useful for modulating and normalising an impaired haemostatic balance in a mammal. In particular, the pharmaceutical composition may be useful for the treatment of coagulation-related diseased states.

More particularly, the pharmaceutical composition may be useful as an inhibitor of blood coagulation in a mammal, as an inhibitor of clotting activity in a mammal, as an inhibitor of deposition of fibrin in a mammal, as an inhibitor of platelet deposition in a mammal, in the treatment of mammals suffering from deep vein thrombosis, pulmonary embolism, stroke, disseminated intravascular coagulation (DIC), vascular restenosis, platelet deposition and associated disorders, myocardial infarction, angiogenesis, tumour growth, tumour invasion, metastasis, and in the prophylactic treatment of mammals with atherosclerotic vessels at risk for developing thrombosis.

The present invention is further illustrated by the following examples.

EXAMPLE

Example 1

FVIIa/TF Amidolytic Assay:

Compound solutions and buffer are the same as in the above FX activation assay. 150 microliters of FVIIa (13.3 nM in buffer), 20 microliters of soluble TF (250 nM in buffer), 10 microliters of test compound (various concentrations in DM80) and 20 microliters of substrate S-2288 (10 mM in water) is mixed in microtiter plate well. This gives final concentrations of FVIIa, TF and S-2288 of 10 nM, 25 nM and 1 mM, respectively. The absorbance at 405 nm is measured continuously for 20 minutes. The degree of inhibition is calculated from the slope of the absorbance curve compared to the curve obtained when using DMSO without test compound.

Example 2

FXa Amidolytic Assay:

Compound solutions and buffer are the same as in the above FX activation assay. 170 microliters of FXa (1.17 nM in buffer), 10 microliters of test compound (various concentrations in DMSO) and 20 microliters of substrate S-2765 (10 mM in water) is mixed in a microtiter plate well. This gives final concentrations of FXa and S-2765 of 1 nM and 1 mM, respectively. The absorbance at 405 nm is measured continuously for 20 minutes. The degree of inhibition is calculated from the slope of the absorbance curve compared to the curve obtained when using DMSO without test compound.

Example 3

Inhibitory Compounds are Identified in a FX Activation Assay:

The compounds are dissolved in DMSO and mixed with a solution of FVIIa in $Ca^{2+}$-containing buffer (1+5). 30 $\mu$l of this mixture was then mixed with 45 $\mu$l TF (relipidated in PC/PS vesicles) and 25 $\mu$l of a solution containing FX, all in $Ca^{2+}$-containing buffer. This gives final concentrations of 100 pM FVIIa, 5 pM TF, 175 nM FX and various concentrations of the compounds. After a 5-min incubation, the FVIIa/TF-catalyzed activation of FX is terminated by the addition of 50 $\mu$l buffer containing enough EDTA to give an excess over the $Ca^{2+}$ ions present 50 $\mu$l of a 2-mM solution of S-2765 (FXa substrate) is then added and the FXa formed is allowed to hydrolyze the substrate for 10 minutes during which the absorbance at 405 nm is continuously monitored in a SPECTRAmax™ 340 plate reader. The slope of the absorption curve is compared to that of a control where DMSO alone was added to FVIIa/TF/FX.

Example 4

Test of Anticoagulant Potency in a FVIIa/TF-initiated Clotting Assay:

The test compounds, 20 mM in DMSO, are diluted in citrated normal human plasma just before the analysis (1+19) and placed in the sample carousel. 55 $\mu$l sample (compound in plasma) is mixed with 55 $\mu$l of thromboplastin (Innovin, Dade) and incubated for 5 min. The clotting reaction is started by adding 55 $\mu$l of a 25-mM $CaCl_2$ solution, yielding a final compound concentration of 0.33 mM. The clotting time is measured using an ACL 300 R coagulometer. The ratio between the clotting time in the presence and absence of test compound is used to quantify the anticoagulant efficiency.

Examples 5–22

The inhibitory effect of several representative compounds are tested in a) the FX activation assay of example 3,
b) the FXa amidolytic assay of example 2,
c) the TF/FVIIa amidolytic assay of example 1.

Compounds having an IC50 of <20 $\mu$M in a), IC50>100 $\mu$M in b), and IC50>100 $\mu$M in c) are selected, and the anticoagulant potency is tested in a FVIIa/TF-induced plasma clotting assay. The selected compounds show a clot ratio>1.

| Ex. No. | Structure | TF/FVII/FX (FX activation) IC50 FXa (μM) | IC50 TF/FVIIa (μM) | FX amidolytic IC50 FX (μM) | Clot ratio |
|---|---|---|---|---|---|
| 5 | 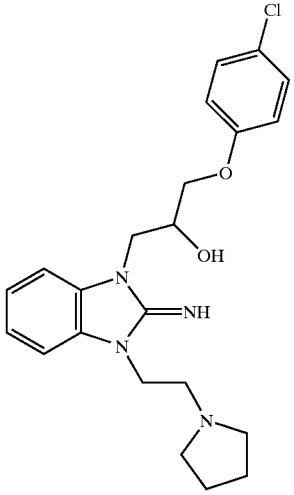<br>1-(4-Chloro-phenoxy)-3-[2-imino-3-(2-pyrrolidin-1-yl-ethyl)-2,3-dihydro-benzoimidazol-1-yl]-propan-2-ol | 18 | >200 | >200 | >3 |
| 6 | 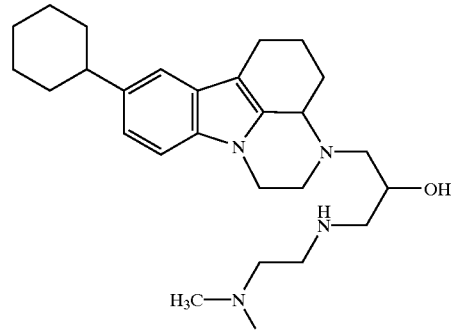<br>1-(8-Cyclohexyl-1,2,3a,4,5,6-hexahydro-pyrazino[3,2,1-jk]carbazol-3-yl)-3-(2-dimethylamino-ethylamino)-propan-2-ol | 17 | >200 | >200 | >3 |
| 7 | 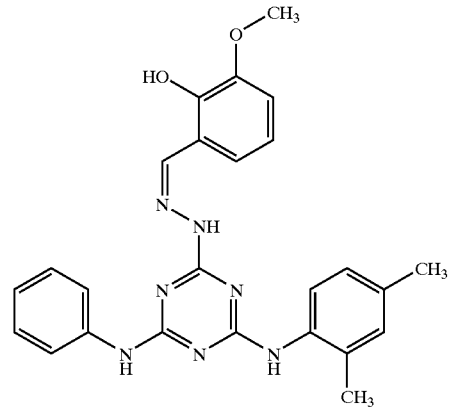<br>2-{[4-(2,4-Dimethyl-phenylamino)-6-phenylamino-[1,3,5]triazin-2-yl]-hydrazonomethyl}-6-methoxy-phenol | 17 | >200 | >200 | 1.03 |

-continued
| 8 | 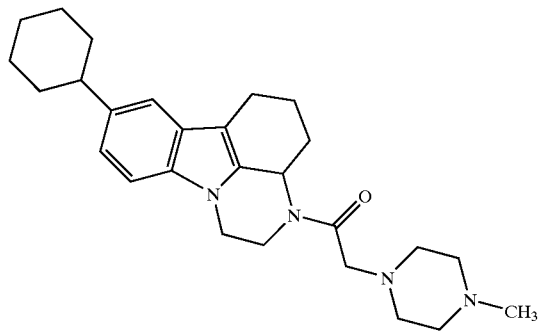 1-(8-Cyclohexyl-1,2,3a,4,5,6-hexahydro-pyrazino[3,2,1-jk]carbazol-3-yl)-2-(4-methyl-piperazin-1-yl)-ethanone | 14 | >200 | >200 | 2.72 |
|---|---|---|---|---|---|
| 9 | 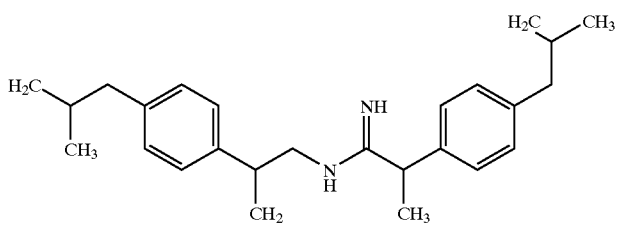 2-(4-Isobutyl-phenyl)-N-[2-(4-isobutyl-phenyl)-propyl]-propionamidine | 11 | >200 | >200 | >3 |
| 10 | 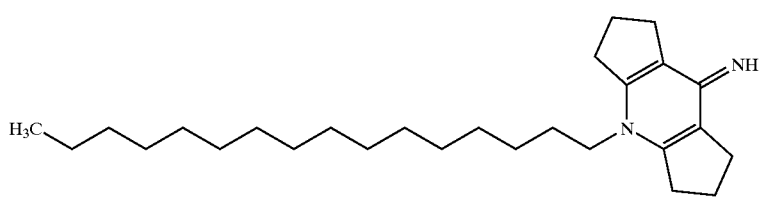 4-Hexadecyl-2,3,4,5,6,7-hexahydro-1H-4-aza-s-indacen-8-ylideneamine | 7.7 | >200 | >200 | 2.84 |
| 11 | 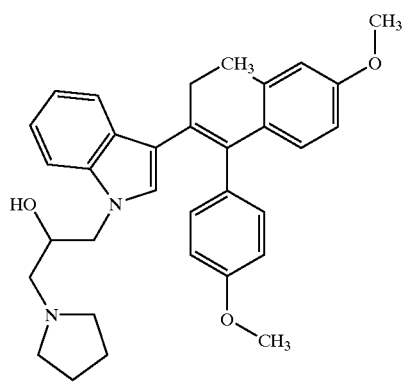 1-{3-[1-Ethyl-2,2-bis-(4-methoxy-phenyl)-vinyl]-indol-1-yl}-3-pyrrolidin-1-yl-propan-2-ol | 7.7 | >200 | >200 | 1.64 |

-continued
| | | | | | |
|---|---|---|---|---|---|
| 12 | 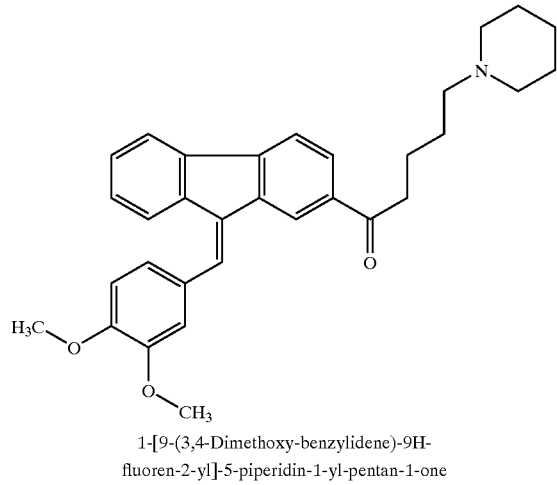<br>1-[9-(3,4-Dimethoxy-benzylidene)-9H-fluoren-2-yl]-5-piperidin-1-yl-pentan-1-one | 7 | >200 | >200 | 1.2 |
| 13 | 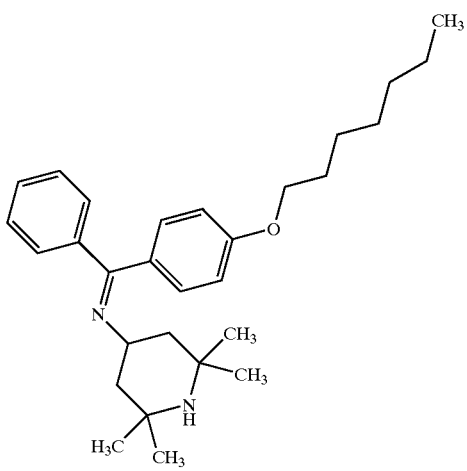<br>[(4-Heptyloxy-phenyl)-phenyl-methylene]-(2,2,6,6-tetramethylpiperidin-4-yl)-amine | 5.8 | >200 | >200 | 2.06 |
| Example No. | Chemical name | Compound | IC50 (μM) FX activation by FVIIa/TF |
|---|---|---|---|
| 14 | N-[7-chloro-2-(4-phenyl-buta-1,3-dienyl)-quinazolin-4-yl]-5-N,N-diethyl-aminopentane-2-amine | 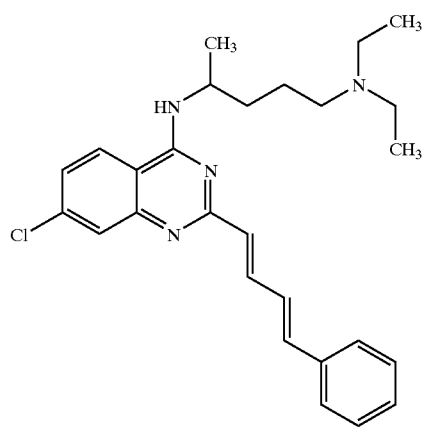 | <20 |

| | | | |
|---|---|---|---|
| 15 | N4-{7-chloro-2-[2-(2,4-dibromo-phenyl)-vinyl]-quinazolin-4-yl}-N1,N1-diethyl-pentane-1,4-diamine | 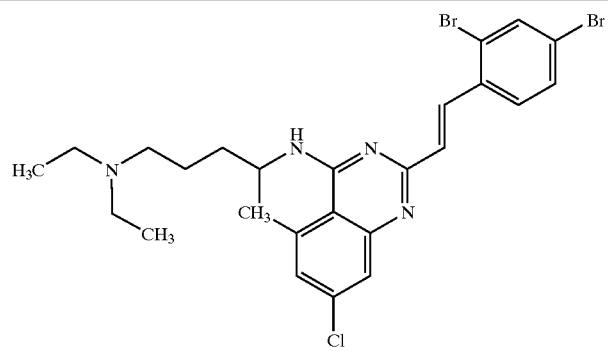 | <20 |
| 16 | N4-{2-[2-(4-bromo-phenyl)-vinyl]-7-chloro-quinazolin-4-yl}-N1,N1-diethyl-pentane-1,4-diamine | 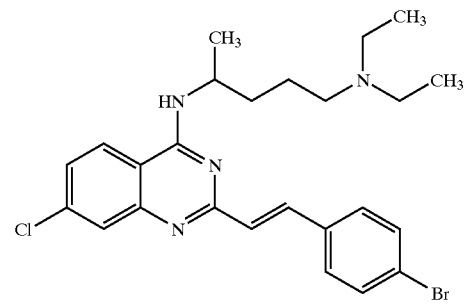 | <20 |
| 17 | N-[5-benzyloxy-6-chloro-1-(3,4-dichlorobenzyl)-1H-indol-3-ylmethyl]-N,N'N'-trimethylpropan-1,3-diamine | 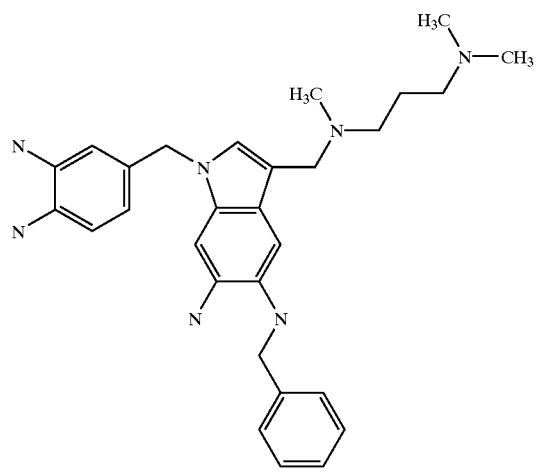 | <20 |
| 18 | N-[5-benzyloxy-1H-indol-3-ylmethyl]-4-dimethylaminopiperidine | 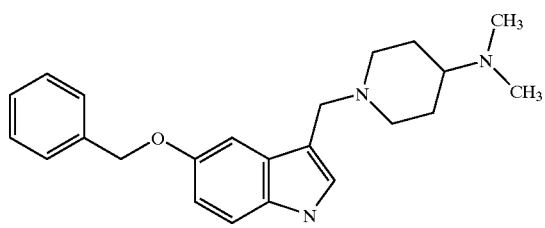 | <20 |
| 19 | 2-(3-amino-3,3-bis-phosphono-propionylamino)-3-(1H-indol-3-yl)-propionic acid | 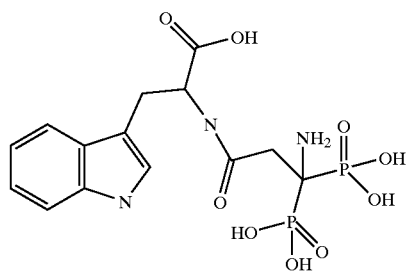 | <20 |

| | | | |
|---|---|---|---|
| 20 | N-[5-benzyloxy-1-(3,4-dichlorobenzyl)-1H-indole-2-carboxylic acid(3-dimethylaminopropyl)amide | 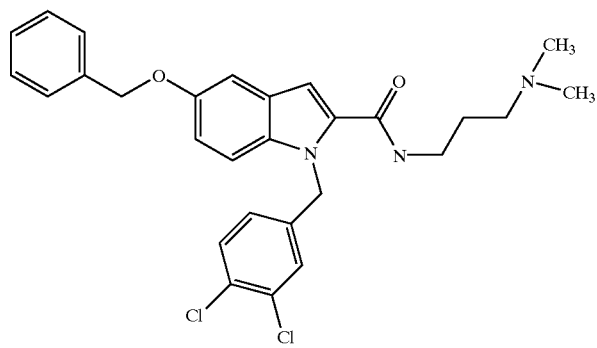 | <20 |
| 21 | N,N-dimethyl-1-(3,4-dichlorobenzyl)-5-benzyloxy-6-chlorotrypamine | 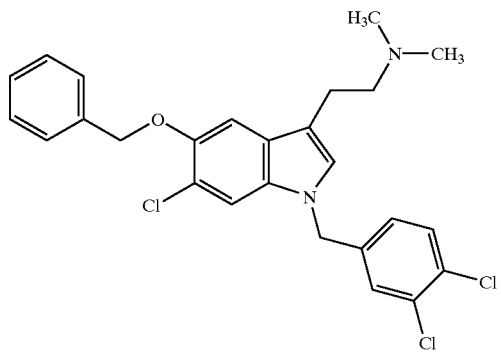 | <20 |
| 22 | 1-{3-[1-ethyl-2,2-bis-(4-methoxy-phenyl)-vinyl]-indol-1-yl}-3-pyrrolidin-1-yl-propan-2-ol | 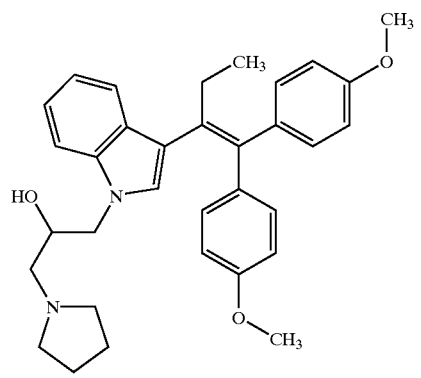 | <20 |

What is claimed is:

1. A compound having an inhibitory action on Factor VII-Tissue Factor (FVII-TF) activity, wherein said compound exhibits:
   (i) half-maximal inhibition at a concentration of 20 μM or less in a FX activation assay,
   (ii) half-maximal inhibition at a concentration of 100 μM or more in a FXa amidolytic assay, and
   (iii) half-maximal inhibition at a concentration of 20 μM or more in a TF/FVIIa amidolytic assay.

2. A compound as defined in claim 1, wherein said compound further exhibits clotting activity corresponding to a clot ratio of more than 1 in a FVIIa/TF-initiated clotting assay.

3. A pharmaceutical composition comprising a compound as defined in claim 1 and a pharmaceutically acceptable carrier or excipient.

4. A method for treatment of a FVIIa/TF-related disease or disorder in a subject, which method comprises administering an effective amount of at least one compound according to claim 1 to a subject in need of such treatment.

5. A method according to claim 4, wherein the FVIIa/TF-related disease or disorder is selected from the group consisting of: deep venous thrombosis, arterial thrombosis, post surgical thrombosis, coronary artery bypass graft (CABG), percutaneous transdermal coronary angioplastry (PTCA), stroke, tumour metastasis, angiogenesis, thrombolysis, arteriosclerosis and restenosis following angioplastry, inflammation, septic chock, septicemia, hypotension, adult respiratory distress syndrome (ARDS), disseminated intravascular coagulopathy (DIC), pulmonary embolism, platelet deposition, myocardial infarction, and a disease or disorder requiring one or more of dialysis procedures, blood filtration, or blood bypass during surgery.

* * * * *